US007977081B2

(12) United States Patent
Van Den Heuvel et al.

(10) Patent No.: US 7,977,081 B2
(45) Date of Patent: Jul. 12, 2011

(54) RECOMBINANT CARBOXYPEPTIDASE B

(75) Inventors: Joop Van Den Heuvel, Wolfenbuettel (DE); Joerg Bartuch, Wolfenbuettel (DE); Arno Cordes, Salzgitter (DE)

(73) Assignee: Merck Biosciences AG (CH)

( * ) Notice: Subject to any disclaimer, the term of this patent is extended or adjusted under 35 U.S.C. 154(b) by 659 days.

(21) Appl. No.: 11/663,404

(22) PCT Filed: Sep. 26, 2005

(86) PCT No.: PCT/EP2005/054806

§ 371 (c)(1), (2), (4) Date: Jul. 21, 2008

(87) PCT Pub. No.: WO2006/035008

PCT Pub. Date: Apr. 6, 2006

(65) Prior Publication Data

US 2008/0311619 A1 Dec. 18, 2008

(30) Foreign Application Priority Data

Sep. 27, 2004 (EP) .................................... 04104696

(51) Int. Cl.

| | |
|---|---|
| ***C12N 9/48*** | (2006.01) |
| ***C12N 15/57*** | (2006.01) |
| ***C12N 15/62*** | (2006.01) |
| ***C12N 15/74*** | (2006.01) |
| ***C12N 15/79*** | (2006.01) |
| ***C12N 15/85*** | (2006.01) |
| *C12N 15/81* | (2006.01) |

(52) U.S. Cl. .................... 435/212; 435/69.7; 435/252.3; 435/254.11; 435/254.23; 435/320.1

(58) Field of Classification Search ........................ None
See application file for complete search history.

(56) References Cited

U.S. PATENT DOCUMENTS

| | | | | |
|---|---|---|---|---|
| 5,206,161 | A * | 4/1993 | Drayna et al. | 435/212 |
| 5,364,934 | A * | 11/1994 | Drayna et al. | 536/23.2 |
| 5,672,496 | A * | 9/1997 | Fayerman et al. | 435/212 |
| 5,945,329 | A * | 8/1999 | Breddam et al. | 435/223 |
| 5,948,668 | A * | 9/1999 | Hartman et al. | 435/212 |
| 5,985,627 | A * | 11/1999 | Mortensen et al. | 435/129 |
| 6,140,100 | A * | 10/2000 | Smith et al. | 435/226 |
| 6,187,579 | B1 * | 2/2001 | Breddam et al. | 435/223 |
| 6,436,691 | B1 * | 8/2002 | Slater et al. | 435/226 |
| 6,455,294 | B1 * | 9/2002 | Gan et al. | 435/212 |
| 6,531,294 | B1 * | 3/2003 | Habermann | 435/68.1 |
| 6,656,718 | B2 * | 12/2003 | Begent et al. | 435/212 |
| 7,060,266 | B1 * | 6/2006 | Matsumoto | 424/94.63 |
| 2002/0009734 | A1 * | 1/2002 | Halsted et al. | 435/6 |
| 2004/0136976 | A1 * | 7/2004 | Smolyar | 424/94.63 |
| 2008/0175834 | A1 * | 7/2008 | Cronet et al. | 424/94.63 |

FOREIGN PATENT DOCUMENTS

| | | |
|---|---|---|
| EP | 1538203 | 6/2005 |
| WO | WO 97/07769 | 3/1997 |

OTHER PUBLICATIONS

Marx, P. F., et al., 2004, "Generation and characterization of a highly stable form of activated thrombin-activatable fibrinolysis inhibitor", The Journal of Biological Chemistry, vol. 279, No. 8, pp. 6620-6628.*

Database Uniprot Online, Mar. 1, 1989, *Carboxypeptidase B Precursor* (*EC 3.4.17.2*), 2 pps.

Database Geneseq Online, Aug. 24, 1993, "*Human Plasma Carboxypeptidase B*."; 2 pps.

Ventura, et al.,*Mapping the Pro-region of Carboxypeptidase B by Protein Engineering. Cloning, Overexpression, and Mutagenesis of the Porcine Proenzyme*, Journal of Biological Chemistry, vol. 274, No. 28, Jul. 9, 1999, pp. 19925-19933.

Su-Xia, et al., "*Cloning and Expression of a New Rat Procarboxypeptidase B Gene in Escherichia coli and Purification of Recombination Carboxypeptidase B*", Protein and Peptide Letters, vol. 10, No. 6, pp. 581-590, 2003.

* cited by examiner

*Primary Examiner* — Nashaat T Nashed
*Assistant Examiner* — William W Moore
(74) *Attorney, Agent, or Firm* — Ohlandt, Greeley, Ruggiero & Perle, LLP

(57) ABSTRACT

A nucleic acid coding for pro-carboxypeptidase B (Pro-CPB), comprising three segments A, B and C, wherein at least one of the segments has one of the sequences according to SEQ ID No. 1, 2 or 3.

10 Claims, No Drawings

SEQUENCE LISTING

```
<160> NUMBER OF SEQ ID NOS: 18

<210> SEQ ID NO 1
<211> LENGTH: 413
<212> TYPE: DNA
<213> ORGANISM: Artificial Sequence
<220> FEATURE:
<223> OTHER INFORMATION: CPB-Fragment

<400> SEQUENCE: 1

acgaggaatt ccatatgcac cactctggtg aacacttcga aggtgaaaag gttttcagag      60

ttaacgttga agacgaaaac cacattaaca ttttgcacga attggcttct actactcaaa     120

ttgacttctg gaagccagac tctgttactc aaattaagcc acactctact gttgacttca     180

gagttaaggc tgaagacatt ttgactgttg aagacttctt gaagcaaaac gaattgcaat     240

acgaagtttt gattaacaac ttgagatcag ttttggaagc tcaattcgac tccagagtta     300
```

gaactactgg tcactcttac gaaaagtaca acaactggga aactattgaa gcatggactc 360
aacaagttac ttctgaaaac ccagacttga tttctagaag cgctattggt acc 413

<210> SEQ ID NO 2
<211> LENGTH: 442
<212> TYPE: DNA
<213> ORGANISM: Artificial Sequence
<220> FEATURE:
<223> OTHER INFORMATION: CPB-Fragment

<400> SEQUENCE: 2
actttcgaag gtagaactat ttacttgttg aaggttggta agccaggttc taacaagcca 60
gctattttca tggactgtgg tttccacgct agagaatgga tttctccagc tttctgtcaa 120
tggttcgtta gagaagctgt tagaacttac ggtagagaaa ttcacatgac tgaattgttg 180
gacaagttgg acttctacgt tttgccagtt ttgaacattg acggttacat ttacacttgg 240
actaagaaca gaatgtggag aaagactagg tctactaacg ctggttcttc ttgtactggt 300
actgacccaa acagaaactt cgacgctggt tggtgttcta ttggtgcttc aagaaaccca 360
tgtgacgaaa cttactgtgg ttctgctgct gaatctgaaa aggaaactaa ggctttggct 420
gacttcatta gaaacaactt gt 442

<210> SEQ ID NO 3
<211> LENGTH: 386
<212> TYPE: DNA
<213> ORGANISM: Artificial Sequence
<220> FEATURE:
<223> OTHER INFORMATION: CPB-Fragment

<400> SEQUENCE: 3
cgactattaa ggcttacttg actattcact cttactctca aatgatgttg tacccatact 60
cttacgacta caagttgcca gaaaacaacg ctgaattgaa cgctttggct aaggctactg 120
ttaaggaatt ggcttctttg cacggtacta agtattctta cggtccaggt gctactacta 180
tttacccagc tgctggtggt tctgacgact gggcttacga ccaaggtatt aagtactctt 240
tcactttcga attgagagac aagggtagat acggtttcgt tttgccagaa tctcaaattc 300
aaccaacttg tgaagaaact atgttggcta ttaagtacgt tacttcttac gttttggaac 360
acttgtacta accatggatc cagagc 386

<210> SEQ ID NO 4
<211> LENGTH: 413
<212> TYPE: DNA
<213> ORGANISM: Sus scrofa

<400> SEQUENCE: 4
acgaggaatt ccatatgcac cactctggtg aacacttcga aggtgaaaag gttttcagag 60
ttaacgttga agacgaaaac gacatttctg aattgcacga attggcttct actagacaaa 120
ttgacttctg gaagccagac tctgttactc aaattaagcc acactctact gttgacttca 180
gagttaaggc tgaagacatt ttggctgttg aagacttctt ggaacaaaac gaattgcaat 240
acgaagtttt gattaacaac ttgagatcag ttttggaagc tcaattcgac tccagatgta 300
gaactactgg tcactcttac gaaaagtaca acaactggga aactattgaa gcatggactg 360
aacaagttac ttctaagaac ccagacttga tttctagaag cgctattggt acc 413

<210> SEQ ID NO 5
<211> LENGTH: 442

<212> TYPE: DNA
<213> ORGANISM: Sus scrofa

<400> SEQUENCE: 5
actttcgacg gtgacaacat ttacttgttg aaggttggta agccaggttc taacaagcca 60
gctattttca tggactgtgg tttccacgct agagaatgga tttctcaagc tttctgtcaa 120
tggttcgtta gagacgctgt tagaacttac ggttacgaag ctcacatgac tgagttcttg 180
gacaacttgg acttctacgt tttgccagtt ttgaacattg acggttacat ttacacttgg 240
actaagaaca gaatgtggag aaagactagg tctactaacg ctggttcttc ttgtactggt 300
actgacccaa acagaaactt caacgctggt tggtgtactg ttggtgcttc tgtgaaccca 360
tgtaacgaaa cttactgtgg ttctgctgct gaatctgaaa aggaaactaa ggctttggct 420
gacttcatta gaaacaactt gt 442

<210> SEQ ID NO 6
<211> LENGTH: 383
<212> TYPE: DNA
<213> ORGANISM: Sus Scrofa

<400> SEQUENCE: 6
cgactattaa ggcttacttg actattcact cttactctca aatgattttg tacccatact 60
cttacgacta caagttgcca gaaaacgacg ctgaattgaa ctctttggct aagggtgctg 120
ttaaggaatt ggcttctttg tacggtactt cttactctta cggtccaggt tctactacta 180
tttacccagc tgctggtggt tctgacgact gggcttacaa ccaaggtatt aagtactctt 240
tcactttcga attgagagac aagggtagat tcggtttcgt tttgccagaa tctcaaattc 300
aagctacttg tcaagaaact atgttggctg ttaagtacgt tactaactac actttggaac 360
acttgtaacc atggatccag agc 383

<210> SEQ ID NO 7
<211> LENGTH: 402
<212> TYPE: PRT
<213> ORGANISM: Artificial Sequence
<220> FEATURE:
<223> OTHER INFORMATION: new CPB

<400> SEQUENCE: 7

His His Ser Gly Glu His Phe Glu Gly Glu Lys Val Phe Arg Val Asn
1               5                   10                  15

Val Glu Asp Glu Asn His Ile Asn Ile Leu His Glu Leu Ala Ser Thr
            20                  25                  30

Thr Gln Ile Asp Phe Trp Lys Pro Asp Ser Val Thr Gln Ile Lys Pro
        35                  40                  45

His Ser Thr Val Asp Phe Arg Val Lys Ala Glu Asp Ile Leu Thr Val
    50                  55                  60

Glu Asp Phe Leu Lys Gln Asn Glu Leu Gln Tyr Glu Val Leu Ile Asn
65                  70                  75                  80

Asn Leu Arg Ser Val Leu Glu Ala Gln Phe Asp Ser Arg Val Arg Thr
                85                  90                  95

Thr Gly His Ser Tyr Glu Lys Tyr Asn Asn Trp Glu Thr Ile Glu Ala
            100                 105                 110

Trp Thr Gln Gln Val Thr Ser Glu Asn Pro Asp Leu Ile Ser Arg Ser
        115                 120                 125

Ala Ile Gly Thr Thr Phe Glu Gly Arg Thr Ile Tyr Leu Leu Lys Val
    130                 135                 140

-continued

```
Gly Lys Pro Gly Ser Asn Lys Pro Ala Ile Phe Met Asp Cys Gly Phe
145                 150                 155                 160

His Ala Arg Glu Trp Ile Ser Pro Ala Phe Cys Gln Trp Phe Val Arg
                165                 170                 175

Glu Ala Val Arg Thr Tyr Gly Arg Glu Ile His Met Thr Glu Leu Leu
            180                 185                 190

Asp Lys Leu Asp Phe Tyr Val Leu Pro Val Leu Asn Ile Asp Gly Tyr
        195                 200                 205

Ile Tyr Thr Trp Thr Lys Asn Arg Met Trp Arg Lys Thr Arg Ser Thr
    210                 215                 220

Asn Ala Gly Ser Ser Cys Thr Gly Thr Asp Pro Asn Arg Asn Phe Asp
225                 230                 235                 240

Ala Gly Trp Cys Ser Ile Gly Ala Ser Arg Asn Pro Cys Asp Glu Thr
                245                 250                 255

Tyr Cys Gly Ser Ala Ala Glu Ser Glu Lys Glu Thr Lys Ala Leu Ala
            260                 265                 270

Asp Phe Ile Arg Asn Asn Leu Ser Thr Ile Lys Ala Tyr Leu Thr Ile
        275                 280                 285

His Ser Tyr Ser Gln Met Met Leu Tyr Pro Tyr Ser Tyr Asp Tyr Lys
    290                 295                 300

Leu Pro Glu Asn Asn Ala Glu Leu Asn Ala Leu Ala Lys Ala Thr Val
305                 310                 315                 320

Lys Glu Leu Ala Ser Leu His Gly Thr Lys Tyr Ser Tyr Gly Pro Gly
                325                 330                 335

Ala Thr Thr Ile Tyr Pro Ala Ala Gly Gly Ser Asp Asp Trp Ala Tyr
            340                 345                 350

Asp Gln Gly Ile Lys Tyr Ser Phe Thr Phe Glu Leu Arg Asp Lys Gly
        355                 360                 365

Arg Tyr Gly Phe Val Leu Pro Glu Ser Gln Ile Gln Pro Thr Cys Glu
    370                 375                 380

Glu Thr Met Leu Ala Ile Lys Tyr Val Thr Ser Tyr Val Leu Glu His
385                 390                 395                 400

Leu Tyr


<210> SEQ ID NO 8
<211> LENGTH: 401
<212> TYPE: PRT
<213> ORGANISM: Sus scrofa

<400> SEQUENCE: 8

His His Ser Gly Glu His Phe Glu Gly Glu Lys Val Phe Arg Val Asn
1               5                   10                  15

Val Glu Asp Glu Asn Asp Ile Ser Glu Leu His Glu Leu Ala Ser Thr
            20                  25                  30

Arg Gln Ile Asp Phe Trp Lys Pro Asp Ser Val Thr Gln Ile Lys Pro
        35                  40                  45

His Ser Thr Val Asp Phe Arg Val Lys Ala Glu Asp Ile Leu Ala Val
    50                  55                  60

Glu Asp Phe Leu Glu Gln Asn Glu Leu Gln Tyr Glu Val Leu Ile Asn
65                  70                  75                  80

Asn Leu Arg Ser Val Leu Glu Ala Gln Phe Asp Ser Arg Cys Arg Thr
                85                  90                  95

Thr Gly His Ser Tyr Glu Lys Tyr Asn Asn Trp Glu Thr Ile Glu Ala
            100                 105                 110

Trp Thr Glu Gln Val Thr Ser Lys Asn Pro Asp Leu Ile Ser Arg Ser
```

```
        115                 120                 125

Ala Ile Gly Thr Thr Phe Asp Gly Asp Asn Ile Tyr Leu Leu Lys Val
    130                 135                 140

Gly Lys Pro Gly Ser Asn Lys Pro Ala Ile Phe Met Asp Cys Gly Phe
145                 150                 155                 160

His Ala Arg Glu Trp Ile Ser Gln Ala Phe Cys Gln Trp Phe Val Arg
                165                 170                 175

Asp Ala Val Arg Thr Tyr Gly Tyr Glu Ala His Met Thr Glu Phe Leu
            180                 185                 190

Asp Asn Leu Asp Phe Tyr Val Leu Pro Val Leu Asn Ile Asp Gly Tyr
        195                 200                 205

Ile Tyr Thr Trp Thr Lys Asn Arg Met Trp Arg Lys Thr Arg Ser Thr
    210                 215                 220

Asn Ala Gly Ser Ser Cys Thr Gly Thr Asp Pro Asn Arg Asn Phe Asn
225                 230                 235                 240

Ala Gly Trp Cys Thr Val Gly Ala Ser Val Asn Pro Cys Asn Glu Thr
                245                 250                 255

Tyr Cys Gly Ser Ala Ala Glu Ser Glu Lys Glu Thr Lys Ala Leu Ala
            260                 265                 270

Asp Phe Ile Arg Asn Asn Leu Ser Thr Ile Lys Ala Tyr Leu Thr Ile
        275                 280                 285

His Ser Tyr Ser Gln Met Ile Leu Tyr Pro Tyr Ser Tyr Asp Tyr Lys
    290                 295                 300

Leu Pro Glu Asn Asp Ala Glu Leu Asn Ser Leu Ala Lys Gly Ala Val
305                 310                 315                 320

Lys Glu Leu Ala Ser Leu Tyr Gly Thr Ser Tyr Ser Tyr Gly Pro Gly
                325                 330                 335

Ser Thr Thr Ile Tyr Pro Ala Ala Gly Gly Ser Asp Asp Trp Ala Tyr
            340                 345                 350

Asn Gln Gly Ile Lys Tyr Ser Phe Thr Phe Glu Leu Arg Asp Lys Gly
        355                 360                 365

Arg Phe Gly Phe Val Leu Pro Glu Ser Gln Ile Gln Ala Thr Cys Gln
    370                 375                 380

Glu Thr Met Leu Ala Val Lys Tyr Val Thr Asn Tyr Thr Leu Glu His
385                 390                 395                 400

Leu


<210> SEQ ID NO 9
<211> LENGTH: 441
<212> TYPE: DNA
<213> ORGANISM: Artificial Sequence
<220> FEATURE:
<223> OTHER INFORMATION: CPB-Fragment

<400> SEQUENCE: 9

atgttggcgt tcttgattct tgtgactgtg actctagcat ctgctcatca ttctggtgag      60

cactttgaag gtgagaaggt gttccgtgtc aatgttgaag atgaaaatga catcagctta     120

ctccatgagt tggccagcac caggcagatt gacttctgga aaccagattc tgtcacacaa     180

atcaaacctc acagtacagt tgacttccgc gtgaaagcag aagatatttt ggctgtggaa     240

gactttctgg agcagaatga actacaatat gaggtactca taaacaacct gagatctgtg     300

ctagaggctc agtttgacag cagagtccgt acaactggac acagttatga gaagtacaac     360

aactgggaaa cgatagaggc ttggactaag caagtcacca gtgaaaatcc agacctcatc     420

tctcgcacag ccatcggaac t                                               441
```

<210> SEQ ID NO 10
<211> LENGTH: 442
<212> TYPE: DNA
<213> ORGANISM: Artificial Sequence
<220> FEATURE:
<223> OTHER INFORMATION: CPB-Fragment

<400> SEQUENCE: 10
acatttttag gaaacaatat atacctcctc aaggttggca aacctggacc aaataagcct 60
gccattttca tggactgtgg tttccatgcc agagaatgga tttcccatgc attttgccag 120
tggtttgtga gagaggctgt tctcacctat ggatatgaga gtcacatgac agaattcctc 180
aacaagctag acttttatgt cttgcctgtg ctcaatattg atggctacat ctacacctgg 240
accaagaacc gaatgtggag aaagacccgc tctaccaatg ctggaactac ctgcattggc 300
acagacccca acagaaattt tgatgctggg tggtgcacaa ctggagcctc tacagacccc 360
tgcgatgaga cttactgtgg atctgctgca gagtctgaaa aagagaccaa ggccctggct 420
gattttatac gcaacaacct ct 442

<210> SEQ ID NO 11
<211> LENGTH: 368
<212> TYPE: DNA
<213> ORGANISM: Artificial Sequence
<220> FEATURE:
<223> OTHER INFORMATION: CPB-Fragment

<400> SEQUENCE: 11
cctccatcaa agcatacctg acgatccact catactcaca gatgatactc taccctt att 60 cctatgatta caaactcccc gagaacaatg ctgagttgaa taacctggct aaggctgccg 120
tgaaagaact tgctacactg tatggcacca agtacacata cggcccagga gctacaacaa 180
tctatcctgc tgctgggggc tctgatgact gggcttatga ccaaggaatc aaatattcct 240
tcacctttga actccgggat aaaggcagat atggttttat cctccctgaa tcccagatcc 300
aggcaacctg tgaggaaaca atgctggcca tcaaatacgt aaccaactac gtgctgggcc 360
acctgtaa 368

<210> SEQ ID NO 12
<211> LENGTH: 1241
<212> TYPE: DNA
<213> ORGANISM: Artificial
<220> FEATURE:
<223> OTHER INFORMATION: 1-2-3

<400> SEQUENCE: 12
acgaggaatt ccatatgcac cactctggtg aacacttcga aggtgaaaag gttttcagag 60
ttaacgttga agacgaaaac cacattaaca ttttgcacga attggcttct actactcaaa 120
ttgacttctg gaagccagac tctgttactc aaattaagcc acactctact gttgacttca 180
gagttaaggc tgaagacatt ttgactgttg aagacttctt gaagcaaaac gaattgcaat 240
acgaagtttt gattaacaac ttgagatcag ttttggaagc tcaattcgac tccagagtta 300
gaactactgg tcactcttac gaaaagtaca acaactggga aactattgaa gcatggactc 360
aacaagttac ttctgaaaac ccagacttga tttctagaag cgctattggt accactttcg 420
aaggtagaac tatttacttg ttgaaggttg gtaagccagg ttctaacaag ccagctattt 480
tcatggactg tggtttccac gctagagaat ggatttctcc agctttctgt caatggttcg 540
ttagagaagc tgttagaact tacggtagag aaattcacat gactgaattg ttggacaagt 600

```
tggacttcta cgttttgcca gttttgaaca ttgacggtta catttacact tggactaaga    660
acagaatgtg gagaaagact aggtctacta acgctggttc ttcttgtact ggtactgacc    720
caaacagaaa cttcgacgct ggttggtgtt ctattggtgc ttcaagaaac ccatgtgacg    780
aaacttactg tggttctgct gctgaatctg aaaaggaaac taaggctttg gctgacttca    840
ttagaaacaa cttgtcgact attaaggctt acttgactat tcactcttac tctcaaatga    900
tgttgtaccc atactcttac gactacaagt tgccagaaaa caacgctgaa ttgaacgctt    960
tggctaaggc tactgttaag gaattggctt ctttgcacgg tactaagtat tcttacggtc   1020
caggtgctac tactatttac ccagctgctg gtggttctga cgactgggct tacgaccaag   1080
gtattaagta ctctttcact ttcgaattga gagacaaggg tagatacggt ttcgttttgc   1140
cagaatctca aattcaacca acttgtgaag aaactatgtt ggctattaag tacgttactt   1200
cttacgtttt ggaacacttg tactaaccat ggatccagag c                        1241
```

<210> SEQ ID NO 13
<211> LENGTH: 1238
<212> TYPE: DNA
<213> ORGANISM: Artificial
<220> FEATURE:
<223> OTHER INFORMATION: 1-5-6

<400> SEQUENCE: 13

```
acgaggaatt ccatatgcac cactctggtg aacacttcga aggtgaaaag gttttcagag     60
ttaacgttga agacgaaaac cacattaaca ttttgcacga attggcttct actactcaaa    120
ttgacttctg gaagccagac tctgttactc aaattaagcc acactctact gttgacttca    180
gagttaaggc tgaagacatt ttgactgttg aagacttctt gaagcaaaac gaattgcaat    240
acgaagtttt gattaacaac ttgagatcag ttttggaagc tcaattcgac tccagagtta    300
gaactactgg tcactcttac gaaaagtaca acaactggga aactattgaa gcatggactc    360
aacaagttac ttctgaaaac ccagacttga tttctagaag cgctattggt accactttcg    420
acggtgacaa catttacttg ttgaaggttg gtaagccagg ttctaacaag ccagctattt    480
tcatggactg tggtttccac gctagagaat ggatttctca agctttctgt caatggttcg    540
ttagagacgc tgttagaact tacggttacg aagctcacat gactgagttc ttggacaact    600
tggacttcta cgttttgcca gttttgaaca ttgacggtta catttacact tggactaaga    660
acagaatgtg gagaaagact aggtctacta acgctggttc ttcttgtact ggtactgacc    720
caaacagaaa cttcaacgct ggttggtgta ctgttggtgc ttctgtgaac ccatgtaacg    780
aaacttactg tggttctgct gctgaatctg aaaaggaaac taaggctttg gctgacttca    840
ttagaaacaa cttgtcgact attaaggctt acttgactat tcactcttac tctcaaatga    900
ttttgtaccc atactcttac gactacaagt tgccagaaaa cgacgctgaa ttgaactctt    960
tggctaaggg tgctgttaag gaattggctt ctttgtacgg tacttcttac tcttacggtc   1020
caggttctac tactatttac ccagctgctg gtggttctga cgactgggct tacaaccaag   1080
gtattaagta ctctttcact ttcgaattga gagacaaggg tagattcggt ttcgttttgc   1140
cagaatctca aattcaagct acttgtcaag aaactatgtt ggctgttaag tacgttacta   1200
actacacttt ggaacacttg taaccatgga tccagagc                           1238
```

<210> SEQ ID NO 14
<211> LENGTH: 1238
<212> TYPE: DNA
<213> ORGANISM: Artificial -continued

<220> FEATURE:
<223> OTHER INFORMATION: 4-2-6

<400> SEQUENCE: 14

```
acgaggaatt ccatatgcac cactctggtg aacacttcga aggtgaaaag gttttcagag     60
ttaacgttga agacgaaaac gacatttctg aattgcacga attggcttct actagacaaa    120
ttgacttctg gaagccagac tctgttactc aaattaagcc acactctact gttgacttca    180
gagttaaggc tgaagacatt ttggctgttg aagacttctt ggaacaaaac gaattgcaat    240
acgaagtttt gattaacaac ttgagatcag ttttggaagc tcaattcgac tccagatgta    300
gaactactgg tcactcttac gaaaagtaca acaactggga aactattgaa gcatggactg    360
aacaagttac ttctaagaac ccagacttga tttctagaag cgctattggt accactttcg    420
aaggtagaac tatttacttg ttgaaggttg gtaagccagg ttctaacaag ccagctattt    480
tcatggactg tggtttccac gctagagaat ggatttctcc agctttctgt caatggttcg    540
ttagagaagc tgttagaact tacggtagag aaattcacat gactgaattg ttggacaagt    600
tggacttcta cgttttgcca gttttgaaca ttgacggtta catttacact tggactaaga    660
acagaatgtg gagaaagact aggtctacta acgctggttc ttcttgtact ggtactgacc    720
caaacagaaa cttcgacgct ggttggtgtt ctattggtgc ttcaagaaac ccatgtgacg    780
aaacttactg tggttctgct gctgaatctg aaaaggaaac taaggctttg gctgacttca    840
ttagaaacaa cttgtcgact attaaggctt acttgactat tcactcttac tctcaaatga    900
ttttgtaccc atactcttac gactacaagt tgccagaaaa cgacgctgaa ttgaactctt    960
tggctaaggg tgctgttaag gaattggctt ctttgtacgg tacttcttac tcttacggtc   1020
caggttctac tactatttac ccagctgctg gtggttctga cgactgggct tacaaccaag   1080
gtattaagta ctctttcact ttcgaattga gagacaaggg tagattcggt ttcgttttgc   1140
cagaatctca aattcaagct acttgtcaag aaactatgtt ggctgttaag tacgttacta   1200
actacacttt ggaacacttg taaccatgga tccagagc                           1238
```

<210> SEQ ID NO 15
<211> LENGTH: 1241
<212> TYPE: DNA
<213> ORGANISM: Artificial
<220> FEATURE:
<223> OTHER INFORMATION: 4-5-3

<400> SEQUENCE: 15

```
acgaggaatt ccatatgcac cactctggtg aacacttcga aggtgaaaag gttttcagag     60
ttaacgttga agacgaaaac gacatttctg aattgcacga attggcttct actagacaaa    120
ttgacttctg gaagccagac tctgttactc aaattaagcc acactctact gttgacttca    180
gagttaaggc tgaagacatt ttggctgttg aagacttctt ggaacaaaac gaattgcaat    240
acgaagtttt gattaacaac ttgagatcag ttttggaagc tcaattcgac tccagatgta    300
gaactactgg tcactcttac gaaaagtaca acaactggga aactattgaa gcatggactg    360
aacaagttac ttctaagaac ccagacttga tttctagaag cgctattggt accactttcg    420
acggtgacaa catttacttg ttgaaggttg gtaagccagg ttctaacaag ccagctattt    480
tcatggactg tggtttccac gctagagaat ggatttctca agctttctgt caatggttcg    540
ttagagacgc tgttagaact tacggttacg aagctcacat gactgagttc ttggacaact    600
tggacttcta cgttttgcca gttttgaaca ttgacggtta catttacact tggactaaga    660
acagaatgtg gagaaagact aggtctacta acgctggttc ttcttgtact ggtactgacc    720
```

```
caaacagaaa cttcaacgct ggttggtgta ctgttggtgc ttctgtgaac ccatgtaacg    780

aaacttactg tggttctgct gctgaatctg aaaaggaaac taaggctttg gctgacttca    840

ttagaaacaa cttgtcgact attaaggctt acttgactat tcactcttac tctcaaatga    900

tgttgtaccc atactcttac gactacaagt tgccagaaaa caacgctgaa ttgaacgctt    960

tggctaaggc tactgttaag gaattggctt ctttgcacgg tactaagtat tcttacggtc   1020

caggtgctac tactatttac ccagctgctg gtggttctga cgactgggct tacgaccaag   1080

gtattaagta ctctttcact ttcgaattga gagacaaggg tagatacggt ttcgttttgc   1140

cagaatctca aattcaacca acttgtgaag aaactatgtt ggctattaag tacgttactt   1200

cttacgtttt ggaacacttg tactaaccat ggatccagag c                       1241
```

<210> SEQ ID NO 16
<211> LENGTH: 1238
<212> TYPE: DNA
<213> ORGANISM: Artificial
<220> FEATURE:
<223> OTHER INFORMATION: 1-2-6

<400> SEQUENCE: 16

```
acgaggaatt ccatatgcac cactctggtg aacacttcga aggtgaaaag gttttcagag     60

ttaacgttga agacgaaaac cacattaaca ttttgcacga attggcttct actactcaaa    120

ttgacttctg gaagccagac tctgttactc aaattaagcc acactctact gttgacttca    180

gagttaaggc tgaagacatt ttgactgttg aagacttctt gaagcaaaac gaattgcaat    240

acgaagtttt gattaacaac ttgagatcag ttttggaagc tcaattcgac tccagagtta    300

gaactactgg tcactcttac gaaaagtaca acaactggga aactattgaa gcatggactc    360

aacaagttac ttctgaaaac ccagacttga tttctagaag cgctattggt accactttcg    420

aaggtagaac tatttacttg ttgaaggttg gtaagccagg ttctaacaag ccagctattt    480

tcatggactg tggtttccac gctagagaat ggatttctcc agctttctgt caatggttcg    540

ttagagaagc tgttagaact tacggtagag aaattcacat gactgaattg ttggacaagt    600

tggacttcta cgttttgcca gttttgaaca ttgacggtta catttacact tggactaaga    660

acagaatgtg gagaaagact aggtctacta acgctggttc ttcttgtact ggtactgacc    720

caaacagaaa cttcgacgct ggttggtgtt ctattggtgc ttcaagaaac ccatgtgacg    780

aaacttactg tggttctgct gctgaatctg aaaaggaaac taaggctttg gctgacttca    840

ttagaaacaa cttgtcgact attaaggctt acttgactat tcactcttac tctcaaatga    900

ttttgtaccc atactcttac gactacaagt tgccagaaaa cgacgctgaa ttgaactctt    960

tggctaaggg tgctgttaag gaattggctt ctttgtacgg tacttcttac tcttacggtc   1020

caggttctac tactatttac ccagctgctg gtggttctga cgactgggct tacaaccaag   1080

gtattaagta ctctttcact ttcgaattga gagacaaggg tagattcggt ttcgttttgc   1140

cagaatctca aattcaagct acttgtcaag aaactatgtt ggctgttaag tacgttacta   1200

actacacttt ggaacacttg taaccatgga tccagagc                           1238
```

<210> SEQ ID NO 17
<211> LENGTH: 1241
<212> TYPE: DNA
<213> ORGANISM: Artificial
<220> FEATURE:
<223> OTHER INFORMATION: 1-5-3

<400> SEQUENCE: 17
acgaggaatt ccatatgcac cactctggtg aacacttcga aggtgaaaag gttttcagag 60
ttaacgttga agacgaaaac cacattaaca ttttgcacga attggcttct actactcaaa 120
ttgacttctg gaagccagac tctgttactc aaattaagcc acactctact gttgacttca 180
gagttaaggc tgaagacatt ttgactgttg aagacttctt gaagcaaaac gaattgcaat 240
acgaagtttt gattaacaac ttgagatcag ttttggaagc tcaattcgac tccagagtta 300
gaactactgg tcactcttac gaaaagtaca acaactggga aactattgaa gcatggactc 360
aacaagttac ttctgaaaac ccagacttga tttctagaag cgctattggt accactttcg 420
acggtgacaa catttacttg ttgaaggttg gtaagccagg ttctaacaag ccagctattt 480
tcatggactg tggtttccac gctagagaat ggatttctca agctttctgt caatggttcg 540
ttagagacgc tgttagaact tacggttacg aagctcacat gactgagttc ttggacaact 600
tggacttcta cgttttgcca gttttgaaca ttgacggtta catttacact tggactaaga 660
acagaatgtg gagaaagact aggtctacta acgctggttc ttcttgtact ggtactgacc 720
caaacagaaa cttcaacgct ggttggtgta ctgttggtgc ttctgtgaac ccatgtaacg 780
aaacttactg tggttctgct gctgaatctg aaaaggaaac taaggctttg gctgacttca 840
ttagaaacaa cttgtcgact attaaggctt acttgactat tcactcttac tctcaaatga 900
tgttgtaccc atactcttac gactacaagt tgccagaaaa caacgctgaa ttgaacgctt 960
tggctaaggc tactgttaag gaattggctt ctttgcacgg tactaagtat tcttacggtc 1020
caggtgctac tactatttac ccagctgctg gtggttctga cgactgggct tacgaccaag 1080
gtattaagta ctctttcact ttcgaattga gagacaaggg tagatacggt ttcgttttgc 1140
cagaatctca aattcaacca acttgtgaag aaactatgtt ggctattaag tacgttactt 1200
cttacgtttt ggaacacttg tactaaccat ggatccagag c 1241

<210> SEQ ID NO 18
<211> LENGTH: 1241
<212> TYPE: DNA
<213> ORGANISM: Artificial
<220> FEATURE:
<223> OTHER INFORMATION: 4-2-3

<400> SEQUENCE: 18
acgaggaatt ccatatgcac cactctggtg aacacttcga aggtgaaaag gttttcagag 60
ttaacgttga agacgaaaac gacatttctg aattgcacga attggcttct actagacaaa 120
ttgacttctg gaagccagac tctgttactc aaattaagcc acactctact gttgacttca 180
gagttaaggc tgaagacatt ttggctgttg aagacttctt ggaacaaaac gaattgcaat 240
acgaagtttt gattaacaac ttgagatcag ttttggaagc tcaattcgac tccagatgta 300
gaactactgg tcactcttac gaaaagtaca acaactggga aactattgaa gcatggactg 360
aacaagttac ttctaagaac ccagacttga tttctagaag cgctattggt accactttcg 420
aaggtagaac tatttacttg ttgaaggttg gtaagccagg ttctaacaag ccagctattt 480
tcatggactg tggtttccac gctagagaat ggatttctcc agctttctgt caatggttcg 540
ttagagaagc tgttagaact tacggtagag aaattcacat gactgaattg ttggacaagt 600
tggacttcta cgttttgcca gttttgaaca ttgacggtta catttacact tggactaaga 660
acagaatgtg gagaaagact aggtctacta acgctggttc ttcttgtact ggtactgacc 720
caaacagaaa cttcgacgct ggttggtgtt ctattggtgc ttcaagaaac ccatgtgacg 780
aaacttactg tggttctgct gctgaatctg aaaaggaaac taaggctttg gctgacttca 840

-continued

```
ttagaaacaa cttgtcgact attaaggctt acttgactat tcactcttac tctcaaatga    900

tgttgtaccc atactcttac gactacaagt tgccagaaaa caacgctgaa ttgaacgctt    960

tggctaaggc tactgttaag gaattggctt ctttgcacgg tactaagtat tcttacggtc   1020

caggtgctac tactatttac ccagctgctg gtggttctga cgactgggct tacgaccaag   1080

gtattaagta ctctttcact ttcgaattga gagacaaggg tagatacggt ttcgttttgc   1140

cagaatctca aattcaacca acttgtgaag aaactatgtt ggctattaag tacgttactt   1200

cttacgtttt ggaacacttg tactaaccat ggatccagag c                        1241
```

RECOMBINANT CARBOXYPEPTIDASE B

CROSS-REFERENCE TO RELATED APPLICATIONS

This application is a 371 application of International Application PCT/EP05/054806, filed on Sep. 26, 2005, which claims priority to, and benefit of, European Patent Application No. 04104696.2, filed on Sep. 27, 2004.

BACKGROUND

1. Field of the Invention

The present disclosure relates to pro-carboxypeptidase B and carboxypeptidase B and to a process for preparing them.

2. Discussion of the Background Art

Carboxypeptidase B (CPB) is a pancreatic exopeptidase which cleaves by the hydrolysis of peptide linkages at basic amino acids, such as lysine, arginine and ornithine. The cleavage is effected at the C-terminal end of the polypeptides. It is a zinc-containing peptidase (EC 3.4.17.2).

Carboxypeptidase B is formed from pre-pro-carboxypeptidase B, which is enzymatically inactive. From pre-pro-carboxypeptidase B, a signal peptide is cleaved off to obtain a pro-carboxypeptidase B, which is also enzymatically inactive. From the latter, another peptide is cleaved off to obtain the active carboxypeptidase.

The molecular weight of carboxypeptidase B is about 35 kD. It is employed for a wide variety of purposes, especially for the preparation of peptides, such as insulin, and in protein sequence analysis. Carboxypeptidase B is usually purified from porcine pancreas.

The cDNA sequences of human carboxypeptidase B are known.

WO 96/23064 describes a process for the preparation of recombinant rat carboxypeptidase B. Attempts to express the plasmid described were not successful.

Commercially available carboxypeptidase (purified from natural sources) typically has activities of about 50 to 170 U/mg. One unit (1 U) corresponds to the hydrolysis of 1 mmol of hippuryl-L-Arg per min at 25° C. and at a pH of 7.65.

Carboxypeptidase B purified from natural sources is always contaminated with small amounts of other proteases. Therefore, there is still a need for highly pure carboxypeptidases having an activity as high as possible.

SUMMARY OF THE INVENTION

A novel pro-carboxypeptidase B (pro-CPB) and a novel carboxypeptidase B (CPB), wherein the carboxypeptidases have an enzyme activity of at least 200 U per mg, preferably more than 250 U per mg, more preferably more than 270 U per mg.

The carboxypeptidases are more readily purified. Carboxypeptidase B obtained from porcine pancreas has a purity of 81.6% in reverse-phase HPLC, while the CPB according to the invention has a purity of 97.4%. In gel permeation chromatography, the carboxypeptidases according to the invention have a purity of 99.1% while a carboxypeptidase purified from porcine pancreas has a purity of 77.2%. Surprisingly, the altered structure achieves a higher temperature stability at 40° C. In addition, it shows a higher long-term stability when stored in a liquid form at pH 8.

DETAILED DESCRIPTION OF THE PREFERRED EMBODIMENT

Therefore, on the one hand, the present disclosure relates to a nucleic acid coding for pro-carboxypeptidase B (Pro-CPB) comprising three segments A, B and C, wherein at least one of the segments has one of the sequences according to SEQ ID No. 1, 2 or 3.

In a preferred embodiment, segment A has the sequence according to SEQ ID No. 1, segment B has the sequence of SEQ ID No. 2, and/or segment C has the sequence according to SEQ ID No. 3.

In a further preferred embodiment, at least two of segments A, B and C respectively correspond to one of the sequences having the SEQ ID No. 1, 2 or 3.

In one embodiment, the remaining segments that do not contain any of sequences 1, 2 or 3 are selected from sequences 4 to 6 or 9 to 11.

In one embodiment, at least one of the segments has one of the sequences according to SEQ ID No. 1, 2 or 3, and the sequences are selected from the sequences 1, 4 and 9 for segment A, from 2, 5 and 10 for segment B, and from 3, 6 and 11 for segment C.

Particularly preferred sequences for the nucleic acid coding for pro-carboxypeptidase B are sequences selected from the group consisting of:

SEQ ID No. 1-SEQ ID No. 2-SEQ ID No. 3
SEQ ID No. 1-SEQ ID No. 5-SEQ ID No. 6
SEQ ID No. 4-SEQ ID No. 2-SEQ ID No. 6
SEQ ID No. 4-SEQ ID No. 5-SEQ ID No. 3
SEQ ID No. 1-SEQ ID No. 2-SEQ ID No. 6
SEQ ID No. 1-SEQ ID No. 5-SEQ ID No. 3
SEQ ID No. 4-SEQ ID No. 2-SEQ ID No. 3.

The present disclosure further relates to the pro-carboxypeptidase obtainable by expressing a nucleic acid according to the invention, and to a carboxypeptidase B obtainable by cleaving off the pro sequence of pro-carboxypeptidase B according to the invention. Such a cleavage can be performed, for example, by trypsin.

The present disclosure further relates to an expression vector containing the nucleic acid according to the invention, and to a transformed organism containing the expression vector according to the invention.

The present disclosure further relates to a protein containing an amino acid sequence according to SEQ ID No. 8 with at least 5 mutations selected from the group of D22H, S24N, E25I, R33T, A63T, E69K, C94V, E115Q, K120E, D135E, D137R, N138T, Q168P, D177E, Y184R, A186I, F191L, N194K, N240D, T245S, V246I, V250R, N254D, 1295M, D309N, S314A, G318A, A319T, Y327H, S330K, S337A, N353D, F370Y, A381P, Q384E, V390I, N395S, T397V.

In one embodiment, a Y is appended as amino acid 402.

In a preferred embodiment, the protein according to the present disclosure includes at least seven, more preferably at least ten and most preferably at least fifteen of the above mentioned mutations. The protein may additionally have up to 30 other mutations, deletions or insertions.

Being a recombinant protein, the protein according to the present disclosure is free from contaminations by other natural proteases. In addition, it can be produced in particularly high purity, especially purities of more than 170 U per mg, preferably more than 200 U per mg, more preferably more than 250 U per mg, and most preferably more than 280 U per mg.

The present disclosure further relates to a process for expressing pro-CPB, comprising the steps of:

culturing a transformed organism;
inducing the expression;
purifying the pro-CPB;

and to a process for expressing carboxypeptidase B, comprising the steps of:

culturing a transformed organism according to claim 10;
inducing the expression;
activation by cleaving the pro-CPB into CPB;
purifying the CPB.

The present invention further relates to a carboxypeptidase having the sequence according to SEQ ID No. 7, preferably with a maximum of 30 mutations, deletions or insertions.

"Mutation" means an exchange of an amino acid for another, "insertion" means the additional introduction of a further amino acid, and "deletion" means the removal of an amino acid.

A particularly preferred expression system is Pichia pastoris. However, in principle, other usual expression systems, such as the Baculovirus system in insect cells, or expression in mammal cells may also be employed. The use of the Pichia expression system has been described, for example, in U.S. Pat. No. 5,102,789, which is included herein by reference.

The nucleic acids according to the present disclosure can be synthesized, for example, by chemical synthesis in fragments, and the fragments subsequently ligated. The proteins according to the present disclosure can then be obtained by expressing the corresponding nucleic acid. The nucleic acid may also be obtained by site-directed mutagenesis from the known cDNA sequence of CBP. Methods thereof are described, for example, in The Journal of Biological Chemistry, 174 (1999), 19925-19933, which is included herein by reference.

The present disclosure will be further illustrated by the following further Examples.

The genes were cloned into the following vectors:

| | |
|---|---|
| *Pichia pastoris*: | pKINTEX, pKEXTEX, pPiczα |
| *E. coli*: | Tuner(DE3)pET22-OMPA |
| *Arxula adeninovirans*: | pAL-ALEU2m-GAA 1. |

The highest expression rates were achieved in Pichia pastoris: pKEXTEX-npproCPB.

Culturing Method

A fed-batch method and a continuous method were developed. In these methods, about 200 mg/l of npproCPB was secreted into the medium.

Fed-Batch Culture

Fermentation Medium (for 1 l):

Hexaphosphate Medium 25 g of sodium hexametaphosphate 9 g of ammonium sulfate

Glycerol Salt Medium 45.6 g of glycerol (86%)

18.2 g of potassium sulfate 14.9 g of magnesium sulfate heptahydrate 0.9 g of calcium sulfate dihydrate PTM1 (trace elements) 1 ml/l

| | | |
|---|---|---|
| Glycerol feed (1 l) 314 g (86%) of glycerol | ad 1000 ml with dist. water | autoclave |
| | | after cooling, addition of 9 ml of sterile PTM1 |
| Methanol feed (1 l) 1 l of methanol | | addition of 12 ml of sterile PTM1 |

Culturing Conditions

| | | |
|---|---|---|
| Temperature | 28° C. | |
| Stirring speed, rotations per minute | 500 to 1000 rpm | |
| Culturing time | 90.1 to 138.6 hours | |
| Gas supply | 0.8 to 2 vvm | air |
| Starting volume culture broth | 2 to 8 l | medium and inoculation culture |
| Inoculation volume | 10% of total starting volume | shaking culture |
| Oxygen partial pressure | 6 to 100% | |
| pH value | 4.4 to 7.3 | |

-continued

Course of Culture

| | | |
|---|---|---|
| Glycerol addition | Start: | at an optical density $OD_{600}$ of the culture broth (absorption at 600 nm) of between 15 and 140 |
| | Feeding rate: | between 0.4 and 1.8 ml/min of glycerol feed |
| | Amount fed: | between 4.2 and 16.6% of the starting volume |
| Methanol addition | Start: | at an $OD_{600}$ of between 50 and 195 |
| | Feeding rate: | between 0.04 and 0.2 ml/min for methanol control between 0.1 and 3% methanol content in the culture broth |
| Termination of culture | $OD_{600}$: | between 144.2 and 510 |

Continuous Culture

Medium components of continuous feed (1 l)

| | | |
|---|---|---|
| 9.8 ml of phosphoric acid (75%) | | |
| 0.2 g of calcium chloride dihydrate | | |
| 6 g of potassium sulfate | | |
| 2.28 g of magnesium sulfate heptahydrate | | |
| 1.35 g of potassium hydroxide | in 500 ml of dist. water | |
| 1 ml of Struktol SB2122 | | autoclave |
| 5.4 mg of biotin in solution | | sterile-filtered |
| 2.7 ml of PTM1 | | sterile-filtered |
| 6 ml of ammonia (25%) | | |
| 239 ml of methanol | | |
| | ad 1000 ml with autoclaved distilled water | |

Course of Culture

| | | |
|---|---|---|
| Glycerol addition | Start: | at $OD_{600}$ 16.5 |
| | Feeding rate: | between 1.4 ml/min glycerol feed |
| | Amount fed: | 21.8% of starting volume |
| Methanol addition | Start: | at $OD_{600}$ 126.8 |
| | Feeding rate: | 0.23 ml/min |
| | Amount fed: | 9% of starting volume |
| Continuous feed | Start: | at $OD_{600}$ 130.1 |
| | Feeding rate: | between 20 and 200 ml/h |

Processing Method

1st step: Activation of npproCPB by trypsin cleavage

2nd step: anion-exchange chromatography—DEAE-Sephacel

3rd step: hydrophobic interaction chromatography—butyl-sepharose

This method yields a pure npCPB.

Activation of pronpCPB by Means of Trypsin Cleavage

| | |
|---|---|
| Trypsin from | porcine pancreas 1645 U/mg or porcine pancreas 15,000 U/mg or bovine pancreas 9,280 U/mg |
| Concentration ratios (trypsin:pronpCPB) | between 1:1 and 1:1000 |
| pH values | between pH 6.5 and pH 8.5 |
| Cleavage time | between 10 min and 17 hours |
| Temperature | between 4 and 30° C. |
| Time of activation in the processing | untreated culture supernatant<br>after PEG precipitation and dialysis<br>after DEAE chromatography |

Anion-Exchange Chromatography

| | |
|---|---|
| Anion-exchange gel | DEAE-Sephacel or Q-Sepharose |
| Column volume | 5 to 500 ml |
| Elution buffer | 20 mM Tris/acetate + 0.1 mM of $ZnCl_2$ pH 7.5 or pH 8 |
| Continuous gradient | 0 to 250 mM of NaCl or 0 to 500 mM of NaCl |
| Step gradient | between 500 mM and 1000 mM NaCl |
| Gradient length | between 1 and 5 column volumes |
| Loading (CPB/ml of anion-exchange gel) | between 10 and 64 U/ml |

Hydrophobic Interaction Chromatography (HIC)

| | |
|---|---|
| HIC gel | Toyopearl Butyl 650M |
| Column volume | between 25 and 50 ml |
| Elution buffer | 20 mM of Tris/acetate + 0.1 mM of $ZnCl_2$ pH 7.5 |
| Continuous gradient | 1000 mM to 0 mM of ammonium sulfate |
| Step gradient | 20 mM of Tris/acetate + 0.1 mM of $ZnCl_2$ pH 7.5 |
| Gradient length | between 4 and 10 column volumes |
| Loading (CPB/ml of HIC gel) | between 29.2 and 183 U/ml |

Enzyme Activity

To determine the specific activity of the recombinant carboxypeptidase B (npCPB) and the carboxypeptidase B from porcine pancreas (pigCPB), the following procedure is employed. First, the volume activity of the CPB is determined. as the substrate solution, 0.015 mol of hippurylarginine (Sigma company) is dissolved in 0.05 M Tris/HCl buffer, pH 7.8. Further, a 50 mM Tris/HCl buffer, pH 7.8, is needed. The reaction solution consists of 0.5 ml of Tris buffer, 0.1 ml of the substrate solution and 0.385 ml of distilled water. The reaction is started with 17 μl of CPB enzyme solution. The photometric measurement (ΔE) is effected for 1 min in a silica glass cuvette at a layer thickness of 0.5 cm and at a temperature of 25° C. and at a wavelength of λ=254 nm. The CPB activity is calculated according to the following formula.

$$CPB\,[U/\text{ml}] = \frac{\Delta E \cdot 1002 \cdot \text{dilution}}{0.349 \cdot 0.5 \cdot \text{enzyme solution employed}}$$

The related protein concentration of the enzyme solution is determined by photometry at a wavelength of 280 nm in a silica glass cuvette having a layer thickness of 1 cm and a temperature of between 20 and 25° C. At first, the blank is established by measuring only the absorption of the sample buffer (E(blank)). The sample buffer consists of 0.033 M Tris/HCl, pH 8.0. Then, 0.05 ml of CPB solution is diluted in 3 ml of sample buffer, and the absorption is also determined (E(sample)). The protein concentration is calculated from the following formula.

$$\text{Protein content [mg/ml]} = \frac{10\ \text{g/l} \cdot \Delta E\,(\text{sample})}{21.4} \cdot 61$$

$$\Delta E(\text{sample}) = E(\text{sample}) - E(\text{blank})$$

| Enzyme | Activity | Protein content | Specific activity |
|---|---|---|---|
| npCPB | 92.6 U/ml | 0.31 mg/ml | 298.7 U/mg |
| pigCPB (archive 28754, Merck company) | 244.4 U/ml | 0.94 mg/ml | 260.0 U/mg |

What is claimed is:

1. An isolated nucleic acid coding for a pro-carboxypeptidase B (proCPB) capable of being activated to form a proteolytically active carboxypeptidase B (CPB), wherein the nucleic acid is selected from the group consisting of SEQ ID NO:12; SEQ ID NO:13; SEQ ID NO:14; SEQ ID NO:15; SEQ ID NO:16; SEQ ID NO:17; and SEQ ID NO:18.

2. An isolated pro-carboxypeptidase B obtained by expressing in an isolated microbial cell, or in an insect or mammalian cell line, a nucleic acid coding for a proCPB, wherein the nucleic acid is selected from the group consisting of SEQ ID NO:12; SEQ ID NO:13; SEQ ID NO:14; SEQ ID NO:15; SEQ ID NO:16; SEQ ID NO:17; and SEQ ID NO:18.

3. An isolated carboxypeptidase B obtained by trypsin cleavage of the pro sequence of a proCPB obtained by expressing in an isolated microbial cell, or in an insect or mammalian cell line, a nucleic acid coding for a proCPB selected from the group consisting of SEQ ID NO:12; SEQ ID NO:13; SEQ ID NO:14; SEQ ID NO:15; SEQ ID NO:16; SEQ ID NO:17; and SEQ ID NO:18.

4. The carboxypeptidase according to claim 3, having an enzyme activity of at least 200 U/mg.

5. An expression vector comprising the proCPB-encoding nucleic acid sequence of claim 1.

6. A microbial cell, or in an insect or mammalian cell line, transformed with the expression vector of claim 5.

7. A process for producing a pro-carboxypeptidase B comprising:

culturing the transformed microbial cell, or insect or mammalian cell line, of claim 6;

inducing the expression of the encoded pro-carboxypeptidase B; and purifying the expressed pro-carboxypeptidase B, thereby producing the pro-carboxypeptidase B.

8. A process for producing an active carboxypeptidase B comprising:

culturing the transformed microbial cell, or insect or mammalian cell line, of claim 6;

inducing the expression of the encoded pro-carboxypeptidase B;

activating the expressed proCPB into carboxypeptidase B by cleaving the pro sequence of the proCPB; and purifying the active carboxypeptidase B, thereby producing the carboxypeptidase B.

9. An isolated pro-carboxypeptidase B comprising the amino acid sequence of SEQ ID NO:7.

10. An isolated pro-carboxypeptidase B comprising a modified amino acid sequence of SEQ ID NO:7 having no more than 30 amino acid substitutions, deletions, or insertions.

* * * * *